(12) United States Patent
Apter et al.

(10) Patent No.: US 8,240,850 B2
(45) Date of Patent: Aug. 14, 2012

(54) METHOD FOR DETERMINING THE CONFIGURATION OF AN OPHTHALMIC LENS, OPHTHALMIC LENS PRODUCED ACCORDING TO SAID METHOD, AND METHOD FOR PRODUCING SAID LENS

(76) Inventors: Robert Apter, Chavornay (CH); Alain Apter, Geneva (CH)

( * ) Notice: Subject to any disclaimer, the term of this patent is extended or adjusted under 35 U.S.C. 154(b) by 139 days.

(21) Appl. No.: 12/866,442

(22) PCT Filed: Feb. 5, 2009

(86) PCT No.: PCT/IB2009/050463
§ 371 (c)(1),
(2), (4) Date: Aug. 5, 2010

(87) PCT Pub. No.: WO2009/115932
PCT Pub. Date: Sep. 24, 2009

(65) Prior Publication Data
US 2010/0321635 A1      Dec. 23, 2010

(30) Foreign Application Priority Data

Feb. 6, 2008   (CH) .......................... 161/08
Feb. 22, 2008  (CH) .......................... 255/08
Nov. 20, 2008  (CH) .......................... 1803/08

(51) Int. Cl.
*G02C 7/02*       (2006.01)
(52) U.S. Cl. ................................. 351/159.74
(58) Field of Classification Search ........... 351/159–178
See application file for complete search history.

(56) References Cited

U.S. PATENT DOCUMENTS

| 6,325,510 | B1 * | 12/2001 | Golub et al. | ................. | 351/169 |
| 7,188,949 | B2 * | 3/2007  | Bandhauer et al. | ........... | 351/168 |
| 7,377,641 | B2   | 5/2008  | Piers et al. | | |
| 7,455,404 | B2   | 11/2008 | Bandhauer et al. | | |
| 2006/0098162 | A1 | 5/2006 | Bandhauer et al. | | |
| 2006/0244906 | A1 | 11/2006 | Piers et al. | | |
| 2009/0195748 | A1 | 8/2009 | Bandhauer et al. | | |

FOREIGN PATENT DOCUMENTS

EP       1 424 049         6/2004

OTHER PUBLICATIONS

International Search Report issued in PCT/IB2009/050463, mailed Jan. 21, 2010.
English language translation of International Search Report issued in PCT/IB2009/050463, mailed Jan. 21, 2010.
English Language Translation of the Written Opinion issued in PCT/IB2009/050463, mailed Jan. 21, 2010.
Written Opinion issued in PCT/IB2009/050463, mailed Jan. 21, 2010.

* cited by examiner

*Primary Examiner* — Darryl J Collins
(74) *Attorney, Agent, or Firm* — DLA Piper LLP US

(57) ABSTRACT

The invention relates to a method for making an ophthalmic lens intended to correct the visual acuity of a user, comprising the steps of determining the shape of a base optical corrective element, determining the profile of a phase element structure, said determination comprising the steps of defining a desired depth of focus of said ophthalmic lens; calculating the phase distribution to be created at the entrance pupil of the lens, selecting a phase distribution and performing an iterative calculation to obtain the depth of focus, finding the phase which minimizes the differences between the effective phase distribution and the desired phase distribution and of converting the phase data into geometrical data to define the profile of the phase distribution structure and juxtaposing the resulting phase element structure and the base optical corrective element.

20 Claims, 3 Drawing Sheets

METHOD FOR DETERMINING THE CONFIGURATION OF AN OPHTHALMIC LENS, OPHTHALMIC LENS PRODUCED ACCORDING TO SAID METHOD, AND METHOD FOR PRODUCING SAID LENS

TECHNICAL DOMAIN

The present invention relates to a method for determining the configuration of an ophthalmic lens. It also relates to an ophthalmic lens obtained according to this method as well as a method for producing such an ophthalmic lens.

This invention generally refers to ophthalmic lenses with extended depth of focus (E-DOF) and thus correspondent extended depth of field. These hybrid refractive-diffractive lenses use a diffractive phase element (DPE) on one of the surfaces of the lens and an aspheric geometry on the other surface. These lenses allow the selection of the depth of focus, even a very large one, while maintaining an admissible relatively constant resolution on the focus field. The surface carrying the diffractive phase element can be replaced by an aspheric surface with similar optical characteristics. The hybrid lens is then made of two aspheric surfaces. The depth of focus can be created on segments for instance for the near vision and/or for far vision. The near vision generally has a depth of focus and thus a depth of field lower than the far vision. It is therefore possible to obtain a great depth of focus by the increase of the depth of focus for the near vision only.

The method of the invention is applicable to all ophthalmic lenses such as:
- all negative and positive intraocular lenses and all their possible forms; pseudo-phakic IOL, phakic IOL for anterior and posterior chambers as well as toric versions;
- all positive and negative contact lenses and toric ones;
- all positive and negative eyeglass lenses and toric ones;
- all materials used, particularly plastics, glass, hydrogel materials, hydrophobic materials.

PRIOR ART

At present, there are many ophthalmic lenses allowing the correction of different types of vision problems. It is sometimes useful to correct different types of aberrations in these lenses, in particular the spherical aberrations SA, in order to improve visual acuity to the user. One of the important factors for vision correction is the corresponding depth of field and the related depth of focus.

It should be noted that the depth of field and the depth of focus are linked, but should not be confused. They are defined in the following manner.

A "perfect" lens without aberrations allows the definition of a specific plane in the object space, which is precisely the conjugate of the receiving plane (film, camera, retina, sensor, . . . ) on the image side. In the object side, this concerns the object focus plane. When the object is moved, there will be a tolerance on the image plane position to allow an observer to recognize if the image is still properly focalized to a position called focus limit. The depth of focus is defined as the distance on the lens axis, on the image side, where the image dimension, called the lower circle of confusion (COF) if the object becomes distorted, i.e. where the observer recognizes a loss of resolution. The defocalization then becomes clearly discernible. The depth of field is the corresponding distance of the point of the object, on the object side, before the image reaches the maximum tolerable dimension of the defined lower circle of confusion.

Another important factor for the vision correction is the resolution or the modulation transfer function MTF.

Various intraocular lenses IOL are currently produced with a complete, partial or null correction of the spherical aberrations SA of the cornea of the user. A correction, even partial, produces a decrease in depth of focus. Users seem often to be satisfied with increased depth of focus. Therefore not correcting the SA of the cornea (generally positive) increases the depth of field (and the depth of focus). This increase however remains modest, typically of some tenths of a mm. This is essentially obtained in detriment of the modulation transfer function and of the resolution.

The intraocular lens with a partial correction of the cornea spherical aberrations, as well as those without correction, have the advantage of being less sensitive to decentring, tilt and to a change of position when they are implanted in the patients eye.

In contrast, it is known that lenses in which the cornea spherical aberrations are completely corrected by selection of an adapted aspheric surface have a better resolution. On the other hand, they have a depth of focus and therefore a depth of field that is lower. Furthermore they are more sensitive to decentring, tilt and to change of position.

Generally, in the current lenses, the depth of field and the resolution are narrowly linked. The improvement of one of these parameters leads to the degradation of the other one for a lens having a determined power.

Among the intraocular lens with or without a correction of the spherical aberrations, the following can be mentioned:

Technis multifocal ZM 9000 (Advanced Medical Optics, Inc). This is a diffractive intraocular lens made of silicone with an aspheric surface. This lens has been the first commercially available intraocular lens with an aspheric surface that compensates the monochromatic spherical aberrations of the cornea. It has a computed and realized negative spherical aberration to compensate the positive spherical aberration of the cornea. The compensation is calculated for aberration values of SA measured on a population sample and is not targeted for a personalized correction. These lens performances are particularly sensitive to the implant tilt and decentring. The eye-lens visual system, in this case, will have a good resolution and a depth of focus (and thus a depth of field) lower than in the case of a partial or non-corrected spherical aberration of the cornea.

Akreos Adapt Advanced Optics (Bausch & Lomb, Inc) is an asymmetrical, biconvex lens with aspheric frontal and rear surfaces that remove the spherical aberration SA from the lens. Thus the pseudo-phakic eye preserves a positive monochromatic spherical aberration value due to the cornea, which provide an improved depth of focus and creates a certain pseudo-adjustment. Moreover, this lens has a constant power on its total surface that allows it to be more tolerant to alignment errors and to the tilt, than a lens with a negative spherical aberration correction for compensating the aberration SA of the cornea of the user.

Another problem produced by the current ophthalmic lenses, in particular intraocular lenses, is that they present halos or "glares" and ghost images in some situations, in particular during night vision. This is particularly the case for multifocal lenses.

When producing and selecting the intraocular lens to implant in the patient's eye, some uncertainties exist. In particular, manufacturers do not always accurately measure the lens power (or the focal length) and label with paraxial power mostly. For toric, multifocal and other lenses, the uncertainties may be greater since more complex surfaces are treated. During the implantation, tilt, rotation, centering, bending and other positioning errors in the eye can increase the visual acuity degradation. These errors also depend on the lens design and manufacturing.

Other important elements must be considered such as:
eye aberrations change with age;
aberration values depend on the state of crystalline accommodation;
all surgery on the cornea such as an incision may modify its form and the aberrations accordingly.

All these uncertainties create a degradation of the image resolution on the retina (related to the vision quality) and thus it is not surprising that sometimes, an additional correction is needed after the implantation of an intraocular lens. An error of ±1 diopter around the intended value is normal despite the quality of the specialists and modern tools used for the measures and calculations.

Despite the eye standardization, it is necessary to remember that the ocular characteristics vary from one person to another and in an ideal way, it would be useful to accurately adapt the intraocular lens to the specific requirements of the patient.

Typical values are for instance +0.27 µm for the spherical aberration SA of a normal cornea of a young eye. This value can be compensated by a nearly equal value of the crystalline negative spherical aberration (−0.27 µm). With age, the values of the crystalline spherical aberration SA often become positive. For a person in the sixties, a typical value for the entire eye is +0.54 µm. Obviously, the ocular characteristics as well as the aberration values (spherical and higher order aberrations) vary from one person to another.

DISCLOSURE OF THE INVENTION

The present invention intends to avoid drawbacks for the ophthalmic lens of the prior art by offering lenses with an extended depth of field and therefore also an extended depth of focus relatively to the existing commercially available intraocular lenses.

Moreover, the extension of this depth of focus is not performed in detriment of the resolution or modulation transfer function MTF as in the lenses of the prior art. On the contrary, in the lenses of the invention, on the one hand, the resolution/modulation transfer function MTF and on the other hand the depth of focus/depth of field are relatively independent from one another, especially after the implantation when the lens is combined with the eye. This independence is not complete, but rather allows a better control of these parameters independently from one another in comparison to a standard lens.

One of the aims sought by the present invention is therefore to separate, to some extent, the determination of the depth of field/depth of focus on one hand and the resolution/the modulation transfer function on the other hand.

This invention is also intended to preserve the modulation transfer function MTF which is approximately constant over each segment of the depth of focus.

The aims of the invention are achieved by a method for determining the configuration of an ophthalmic lens intended to correct the visual acuity of a user, this method comprising the following steps:
determining the form of a base optical corrective element according to at least one of the following parameters:
the desired power of the ophthalmic lens;
the desired resolution or modulation transfer function;
the desired extent of the correction of the spherical aberrations of said ophthalmic lens;
the desired extent of the correction of the spherical aberrations of the cornea of the user;
the desired extent of the correction of the chromatic aberrations of said ophthalmic lens;
the desired extent of the correction of the chromatic aberrations of the cornea of the user;
the desired extent of the correction of high order aberrations;
determining the profile of a diffractive phase element structure, said determination comprising the following steps:
defining a desired depth of focus of said ophthalmic lens;
calculating the phase distribution to be created at the entrance pupil of the lens, from the desired depth of focus;
finding the phases which minimize the differences between the effective phase distribution and the desired phase distribution;
converting the phase data into geometrical data in order to define the profile of the diffractive phase distribution structure;
juxtaposing the resulting diffractive phase element structure and the base optical corrective element.

The purposes of this invention are also achieved by an ophthalmic lens intended to correct the visual acuity of a user, characterized in that it comprises a base optical corrective element to which a diffractive phase element structure is juxtaposed.

The aims of the invention are also achieved by a production method of an ophthalmic lens whose configuration is determined by the method of any of claims 1 to 8.

The separation between the depth of field and the resolution is made by the introduction of a specific DPE to create the intended depth of focus/depth of field. For this aim a diffractive phase distribution structure will be used, marked as DPE which produces a specifically calculated phase distribution. In practice, the diffractive phase element structure can be replaced by an aspheric surface producing a similar phase distribution. It is therefore possible to use a refractive surface that produces a phase distribution adapted to the creation of an extended depth of focus instead of the diffractive phase distribution DPE structure.

This extension of depth of focus will be performed, generally, with a modulation transfer function MTF which is approximately constant on the determined depth of focus range called here a window or a segment. In practice, the variation of the resolution on the depth of focus will be around a factor which is two or three, but not of any further magnitude.

It should be noted that the increase of the depth of focus can also be obtained by increasing the correction of the longitudinal spherical aberrations. This correction can be negative or positive. If it is positive, it will be added to the positive spherical aberration of the cornea. This will significantly decrease resolution resp. MTF and may be done on large pupil (more than 5 mm diameter).

The diffractive phase element structure, DPE, creates a particular wave front. The thus created light beam has characteristics used herein for the application to ophthalmic lenses and it can be considered a three-dimensional image apodization so as to obtain an extension on the longitudinal axis without significant loss on the transverse axes. As mentioned above, the diffractive phase element structure DPE can sometimes be replaced by a calculated aspheric surface, either by unfolding ("unwraping"), or from polynomials representing the phase (or equivalent distributions), or from phase distributions which allow equivalent results to be obtained.

Values selected on the main parameters of the lens, namely the resolution or modulation transfer function MTF in part, and the depth of focus or depth of field on the other will thus be obtained. These values can cover, amongst others, the ageing effects, tolerances of measurements, calculation, position and others errors which cause the specialists intervention to be needed. The lens must provide an adequate depth of focus in all cases, as well as an adequate resolution/modulation transfer function MTF.

According to a particular aspect of the invention, it is possible to improve the vision or visual acuity of a patient by offering an ophthalmic lens with different depths of focus FD on different windows. The depth of focus can be relatively small on a window for near sight and larger on a window for far sight. Generally the near vision has a depth of focus and thus a depth of field which is smaller than the one of far vision. It is therefore possible to obtain for example an important depth of focus by increasing only the depth of focus of the near vision.

A lens according to the invention allows for obtaining a light tube that largely avoids the ghost images, halos and "glares".

The methods described in this text allow obtaining an ophthalmic lens including a first, front or rear surface, intended to neutralize or extend the aberrations (spherical, chromatic and high order aberrations) of the eye-lens sight system. This surface is generally aspheric. It comprises a front or rear second surface, formed by one or several areas that can be made as phase distribution structures DPE ("Diffractive Phase Element") calculated and realized to extend the depth of field/depth of focus of the eye visual system. These new phase element structures can be identified, calculated, juxtaposed, and created as diffractive surfaces, then converted and made as aspheric surfaces. These diffractive or aspheric structures produce depths of focus, thus depth of field, which are variable and controllable.

The central thickness of the lens will be selected according to the requirements: thin to obtain a reduced incision of the cornea; thick if a thicker lens is required so as to fill the capsular sac better. The characteristics of depth of focus and resolution may be obtained within important ranges of variations of this thickness.

BRIEF DESCRIPTION OF THE DRAWINGS

The present invention and its advantages will be better understood with reference to the attached figures and to the detailed description of a particular embodiment, in which.

EMBODIMENTS

A particular embodiment of the invention is described with reference to the attached figures. This example is based on an intraocular ophthalmic lens IOL (Intraocular lens). It should be noted however that the methods of the invention are also applied to all types of ophthalmic lens such as those mentioned above.

The determination method for the configuration of a lens as described in the present application can be split into three steps. One of these steps comprises the determination of the shape of a base optical corrective element 10 based on parameters such as the desired final power of the ophthalmic lens, the correction or not of the lens aberrations or of the cornea of the user, such as spherical aberrations, chromatic aberrations or high order aberrations, etc. This base optical corrective element can have a flat, convex, concave, aspheric and/or toric surface.

The resulting lens can have a positive, negative or null power; it can also be multifocal or particularly toric.

Another step comprises the determination of the profile of a diffractive phase element structure DPE with the purpose to increase the depth of focus and the depth of field.

The third step is the juxtaposition of the diffractive phase element structure and the base optical corrective element in order to obtain a hybrid ophthalmic lens 11.

Generally, an ophthalmic lens according to the invention can have a face, for instance the rear one, which is a plane, spherical, aspheric or toric face, and it can be used for partially, totally or non compensating the spherical aberrations or other aberrations of the lens or of the cornea of the user. The second lens face, for instance the front face, can comprise a structure for the increasing of the depth of field. It is possible to consider the rear face as one of the faces of the base optical corrective element 10 and the front face as the juxtaposition of this base optical corrective element 10 with the diffractive phase element structure DPE.

It is also possible to invert the lens in such a way that the rear face comprises the diffractive phase element structure DPE. In this case, however, the lens is not simply inverted, but the structure and power determination must be recalculated.

The diffractive phase element structure DPE essentially determines the depth of focus through its calculated modification of the incoming wave-front phase distribution and will be less affected by the selection of aberration correction, unlike the current classic lenses.

Calculation of the Base Optical Corrective Element Shape

Figure 1:
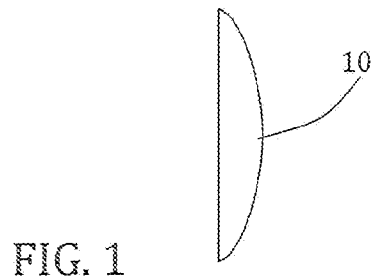
FIG. 1 is a cross sectional view of an example of ophthalmic lens used in the present invention; the convex refractive surface is aspheric and the other surface carrying the diffractive phase distribution structure is flat in this example.

The shape of the base optical corrective element 10 essentially determines the resolution of the lens and of the visual system after implantation. Such a corrective element is disclosed in FIG. 1. This element can be selected, amongst others, according to the following criteria:

the power of the desired lens;
the neutralization of the spherical aberrations SA of the lens. A lens without the spherical aberration SA correction will allow an ocular system to be obtained with a spherical aberration due mostly to the cornea, after implantation;

the creation of a negative spherical aberration SA for the lens IOL. The value of the aberration SA correction will be selected for the entire or partial compensation of the current positive aberration SA of the cornea of the user. This cornea aberration can be measured on the patient or it can correspond to average values selected within a population group. The resolution of the visual system will be optimal if spherical aberrations SA of the ocular system with the lens IOL are non-present. The size of the pupil for such corrections is generally large (more than 5 mm).

the neutralization of other aberrations such as high order aberrations (HOA) or reduction of chromatic aberrations.

It should be noted that the correction of the cornea spherical aberrations SA is not always sought and that other characteristics can be important, for instance the control or the reduction of growth of the epithelial cells by the shape of the surface or by other means, for example square edges.

According to one preferred embodiment, the base optical corrective element 10 may have an aspheric surface. The sagittal distance of such an aspheric surface will be provided by the following known equation:

$$z = \frac{cr^2}{1 + \sqrt{1 - (1+k)c^2r^2}} + \alpha_1 r^2 + \alpha_2 r^4 + \ldots + \alpha_s r^{16} \quad (1)$$

where:
c is the curve in the centre of the surface
k is the conicity
$\alpha_i$ are the polynomial coefficients describing the sagittal distance of the aspheric surface.

The realisation of the aspheric surface to control the phase distribution is therefore possible. Corrections of positive or negative spherical aberrations can be performed, as well as corrections of high order aberrations HOA. The surface profiles as well as the corresponding modulation transfer functions MTF and resolutions can be calculated in different ways, for example with an optical ray tracing program such as Zemax which will also supply the image dimensions, the different Zernike or Seidel coefficients, the chromatic aberrations, etc.

The chromatic dispersion of the eye and of the materials is defined by the Abbe number that uses the wavelengths $\lambda_c$=656.3 nm, $\lambda_d$=587.6 nm and $\lambda_f$=486.1 nm.

Dispersions V(ref) of a refractive element and V(dif) of a diffractive element are respectively determined by:

$V(\text{ref})=(n_d-1)/(n_f-n_c)$ and $$V(\text{dif})=\lambda_d/(\lambda_f-\lambda_c) \quad (2)$$

V(dif) is negative while V(ref) is positive.
For a hybrid lens, one has:

$$P=P(\text{ref})+P(\text{dif}) \quad (3)$$

P(ref) and P(dif) are the powers of the refractive and of the diffractive (phase-control) components respectively.

The chromatic correction is obtained with:

$$(P(\text{ref})/V(\text{ref}))+(P(\text{dif})/V(\text{dif}))=0 \quad (4)$$

V(dif) is negative and constant, (see equation 2), and V(ref) is known. Both equations mentioned above merely calculate two unknown P(ref) and P(dif) to neutralize the chromatic aberrations. These ratios can be integrated in the calculation of the powers of the hybrid lens elements when a chromatic correction is required. By selecting the paraxial powers (which are linked to Abbe numbers), it is possible to reduce or sometimes eliminate the chromatic dispersions.

Depth of Field and Depth of Focus

One of the lens surfaces is used for increasing the depth of focus/depth of field. This surface can be considered as the juxtaposition of the diffractive phase element DPE and the base optical corrective element surface 10. The DPE modifies the phase distribution of the incoming wave-front in a controlled way to produce the researched depth of field/depth of focus.

Figure 3:
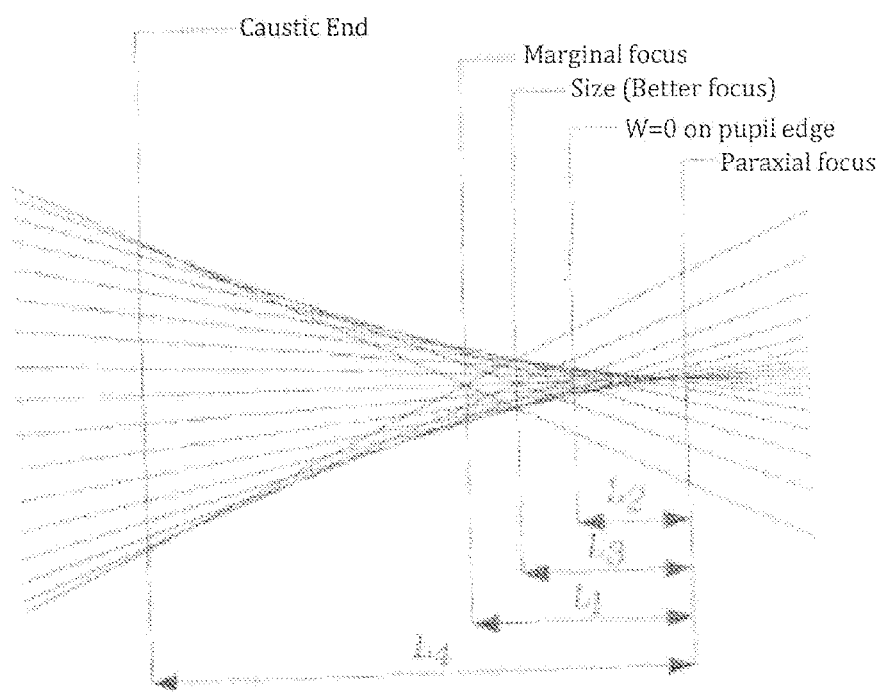
FIG. 3 represents in a schematic way the paths of different ray beams crossing over a lens; the lower circle of confusion COF, the paraxial focus plane and the marginal focus plane are represented.

FIG. 3 is a representation of the optical ray traces respectively in the marginal and paraxial focal planes for conventional lenses; the new invention will extend significantly such effects.

Figure 4:
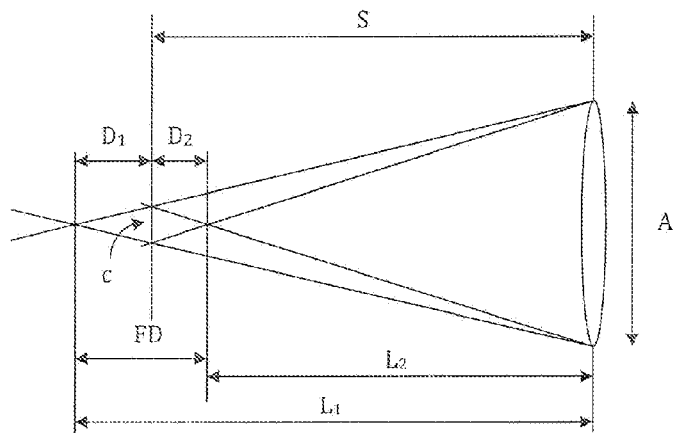
FIG. 4 shows the lens depth of field.

The depth of focus is the product of the diameter C' of the lower circle of confusion (on the film, camera, retina, etc.) allowed by the lens numeric opening (See FIG. 4).

With the geometry of FIG. 4 the following can be obtained:

$$C/A=D1/(S+D1)=D2/(S-D2) \quad (5)$$

where C is the diameter of the lower circle of confusion in the object plane (conjugate of C' defined in the image plane);
D1 and D2 are the acceptable near and far distances of focalization;
A is the lens diameter, or rather the entry pupil diameter;
S is the distance between the focus plane and the lens.

It is therefore possible to obtain:

$$D1=Cs/(A-C) \quad (6)$$

$$D2=Cs/(A+C) \quad (7)$$

D1 is larger than D2 and it will be infinite if A=C. When C is increased, for instance by increasing the spherical aberrations of the lens, D1 increases and D2 decreases. This situation is interesting given that the spherical aberrations are practically always present in the eye-lens system, particularly when the pupil is increased beyond 3 mm.

The distances are:

$$L1=S+D1=AS/(A-C) \quad (8)$$

$$L2=S-D2=AS/(A+C) \quad (9)$$

This is defined on the object side. The prime ' notations are applied on the image side with ratios accordingly adapted.

The lower circle of confusion C' of a perfect lens, limited by the diffraction is generally determined to be given by the Rayleigh criterion by which a deformation of the wave front of $\lambda/4$ is admissible. In practice, C' will be determined from the pixel dimension of a camera or the resolution of the retina or a film, etc. So as to increase C', a spherical aberration C' is frequently introduced that may be substantial. This increases the depth of focus and therefore the depth of field directly and decreases the resolution but always to "modest" extend. (see hereunder)

In an extended depth of focus system C' determines the resolution of the visual system. The corresponding depth of field is determined by the above-mentioned formulas. The distances L1 and L2 can be, for example, the reading distance for L1 and a far distance for L2.

It should be noted that C' can vary within the different segments of the depth of focus. Indeed the peripheral area of the lens gives a value of C' larger than the central area ("marginal focus" in FIG. 3). The resolution of this external area will thus be lower, according to the residual aberrations of the eye-lens sight system. The situation can be complex if the residual spherical aberrations of the eye-lens system are important. FIG. 3 shows the situation, by means of geometrical optics, with the lower circle of confusion, in the focus plane, that is perceived smaller for paraxial rays than for marginal rays for monochromatic illumination ("marginal focus" and "paraxial focus"). The situation is degraded for a polychromatic illumination to determine values of C' that can become important if any chromatic correction is applied. Although the human eye is tolerant and vision is adaptable, it can be advisable to provide some chromatic corrections for important depths of focus and/or for high power domains. The residual aberrations create frequent lower depths of focus with regards to the depths of focus created by the concerned diffractive phase element DPE or by the corresponding aspheric surfaces.

The hyperfocal distance of an optical system is the distance to which the system has to be focused so as to extend the depth of field infinitely. An increase of the depth of field produces a shorter hyperfocal distance so as to have a near vision image, for instance adapted for reading, and an infinitely far vision image. The current intraocular lenses have a limited depth of field created by the lower circle of confusion COF after implantation, due to the resulting spherical aberrations of the system. The typical depth of field values of current usual mono-focal lens, approximately are 2 m or more to infinity. These values depend on residual spherical aberrations of the vision system that will be different for each person, but they can be estimated for a "standard eye".

In a classic way, the Rayleigh criterion gives a depth of focus of $$FD = \pm 2 * \lambda * N^2 \quad (10)$$

where $\lambda$ is the wavelength and
N is the relative opening: focal length/effective pupil diameter.

The total typical value of the depth of focus of a mono-focal IOL is within the range of 0.1 to 0.2 mm. With important spherical aberrations, which deteriorate the visual acuity, the mono-focal lens mentioned above gives depths of focus lower than 0.2 dioptres. A depth of focus of some 0.135 mm corresponds to a distinct sight from the infinity to around 2 meters, at 22 D. These are very low values compared to those obtained with the DPE described here which typically has a value of 2D or more, i.e. some 3 mm at 22 D; this can be computed and realized on any chosen pupil such as: 1 mm, 2 mm, 3 mm.

Calculation of the Phase Distribution Structure

The structure of the phase element DPE can be diffractive or transformed into an aspheric surface, as is explained in detail as follows. The profile determination of this structure depends on the selected depth of focus. For instance, it is possible to select a depth of focus of 1 D, 2 D or more . . . or equivalent values in mm representing the focal depths. The conversion of power into focal lengths and vice versa is well known and depends on differences of the refraction indexes of lens and surrounding environment.

Different depths of focus can be created on different lens areas or windows. For instance, the central part of the lens can be used to create structures to increase the depth of focus for a near vision and the peripheral part of the lens to create some control structures for a far vision or inversely. The number of windows is not limited.

The extension of the depth of focus introduces a spreading of intensities collected by the lens with a defined entry pupil and it reduces the energy density of the image formed on the retina. This may cause compensation by means of the ocular pupil opening increase and by a subconscious learning process of the observation of low intensity images; this may also reduce the image contrast.

In order to create significant depths of focus, essentially Pseudo Non Diffractive Beams (PNDB) or approximations of these types of beams will be used. Non-diffractive electromagnetic wave beams propagating over long distances without any change of dimensions have been defined. These types of beams have a transversal amplitude proportional to J0 ($\alpha\rho$), Bessel function in the order of 0 and of the first type. An ideal beam J0 is propagated in the space without decrement and it radially extends infinitely. The PNDB are an approximation of Bessel beams and are characterized by an almost constant intensity in an axial direction within a set region and by a shape of the beams in the transversal direction. The PNDB have unique characteristics such as a constant axial intensity, extended propagation on the optical axis and a narrow beam. Even with approximations, these beams allow particular optical characteristics to be obtained relative to the divergence, depth of field and resolution.

The following methods linked to the creation of Pseudo Non Diffractive Beams can be applied to the calculation of the diffractive phase element structure DPE of the lens. This DPE will modify the incoming wave-front phase distribution to create an extended depth of focus with the corresponding depth of field extension.

The first step consists in defining the intended depth of focus. The phase distributions of the incoming wave-front are calculated. The phase distribution for a diffractive phase element can be calculated from the following formula, with an even polynomial (or by using the corresponding formula for an odd polynomial).

$$\phi = M \sum_{i=1}^{N} A_i \rho^{2i} \quad (11)$$

where:
($\phi$) is the phase;
$A_i$ is the coefficient of the 2nd power of $\rho$;
$\rho$ is the radial distance
N is the coefficient number of the polynomial;
M is the diffraction order.

Figure 2:
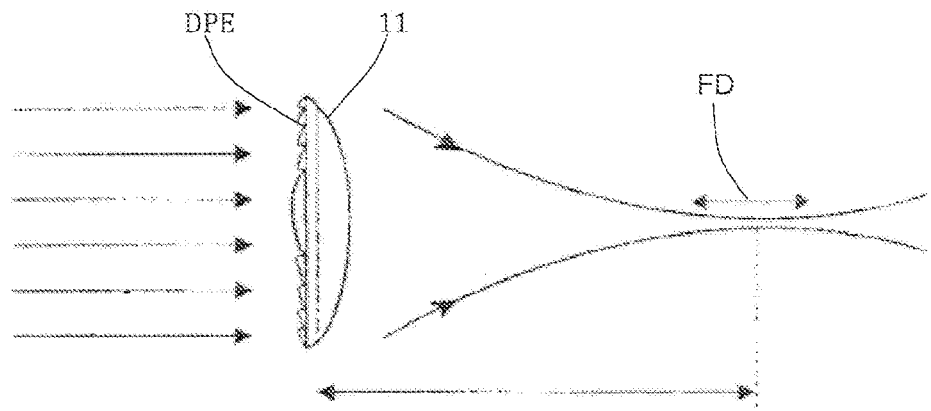
FIG. 2 is a schematic cross sectional view of an ophthalmic lens according to the present invention; other shapes of surfaces are possible.

The phase distribution of the continuous wave-front is then determined by unfolding ("unwrap"). A "light tube" in FIG. 2 represents the depth of focus.

The phase distribution obtained therein is used to obtain the $\alpha$ coefficients of the equation (1) of a wave front with a continuous profile. The number of $\alpha$ coefficients can be selected, if required, with compromises on the wave front profile. The reduction of the number of coefficients will give an approximate but sometimes satisfactory wave front, depending on the number of coefficients and the introduced approximation. A diffractive phase element DPE can therefore be replaced by an aspheric surface. This surface is calculated by a polynomial representing the phase distribution of the wave front. This polynomial can be calculated by the equation (1) providing a function of the thickness (even if possible, but also odd or combined) for a defined wavelength. It is also possible to calculate the phase distribution from an equation giving the phase distribution of the wave front directly, as presented herein.

Specific phase distributions giving extended depth of focus can be sought. Such phase distribution will allow the creation of lenses with E-DOF characteristics. Some interesting phase distribution of optical wave examples are given herein:

$$\phi(r) = (-2\pi/(\lambda^* a))\log(1 + a^*(r^2 - r_1^2)/d_1)$$

with $$a = (d_2 - d_1)/(R^2 - r_1^2) \quad (12)$$

$$\phi(r) = (r/b^* R)^p \quad (13)$$

$r_1$ is the considered ray of the optical surface, $d_1$ and $d_2$ are the front and rear focal lengths.

The linear axicon creates the following phase distribution known to provide extended depth of focus:

$$\phi(r) = a^* r \quad (14)$$

The phase distribution $\phi$ required for creating the extended depth of focus, can be obtained folded or unfolded ("wrap/unwrap") so as to provide a diffractive or refractive-aspheric surface, which is sometimes a complex surface.

The structures of the phase element DPE can be calculated and realized, either by diffractive structures or by an equivalent approximate aspheric surface. The surface selection, either diffractive or aspheric, is related to the production costs and other parameters such as chromatic aberrations, which are important to the diffractive structures. These can be corrected or minimized.

Creating a light beam with a diffractive element can introduce chromatic aberrations and the production tolerances can be critical on parameters such as intensity distributions. The use of an aspheric surface can then be judicious.

The shape of the diffractive phase element DPE can be determined by different methods, for example by an inverted calculation defining the domain of desired focal lengths (or powers) and then calculation of the required phase distribution.

An example of a resulting hybrid lens is presented in FIG. 2.

Let's consider an incident wave-front, proceeding for example from infinity so as to simplify.

The field in the entry plane, Z=0 is the following:

$$U_1(r_1) = \rho_1(r_1)\exp[i\Phi_1(r_1)] \quad (15)$$

At the exit on plane $Z_\alpha$, for the wave function, the following can be obtained:

$$U_2(r_{2\alpha}, z_\alpha) = \rho_2(r_{2\alpha}, z_\alpha)\exp[i\Phi_2(r_{2\alpha}, z_\alpha)] \quad (16)$$

With the paraxial approximation of a system with rotation symmetry, the wave function at the exit is linked to that at the entry by a lineal transformation:

$$U_2(r_{2\alpha}, z_\alpha) = \int G(r_{2\alpha}, r_1, z_\alpha) U_2(r_1) dr_2 \quad (17)$$

where $G(r_{2\alpha}, r_1, Z_\alpha)$ is the transformation function.

In the paraxial approximation, used thereafter, the following Fresnel integral is obtained:

$$G(r_{2\alpha}, r_1, z_\alpha) = \frac{2\pi}{i\lambda z_\alpha}\exp(i2\pi z_\alpha/\lambda) \times \exp[i\pi(r_{2\alpha}^2 + r_1^2)/\lambda z_\alpha] \times J_0\left(\frac{2\pi r_{2\alpha} r_1}{\lambda s_{z\alpha}}\right) r_1 \quad (18)$$

Z is the axial coordinate on the optical axis; $r_1$ and $r_{2\alpha}$ are the radial coordinates at the entry and at exit on the sample plane $\alpha$.

For the resolution and depth of focus we respectively have:

$$\rho = (2\pi/\lambda)(NA)R$$

$$u = (2\pi/\lambda)(NA)^2 Z \quad (19)$$

$\lambda$ is the wavelength, for instance at 550 nm; NA is the numeric aperture; R and Z are the axial and radial coordinates in the focal region.

The aim of calculating the diffractive phase element DPE is to find the phases of this structure DPE which minimize the differences between the effective distribution of the field and the desired one, with selected weighing. The error function is:

$$E = \Sigma_{\alpha=1}^{N2} W(\alpha)\{\Sigma_{m=1}^{N2\alpha}[\tilde{\rho}_{2m\alpha} - |\Sigma_{n=1}^{N2} G_{mn}(z_\alpha)\rho_{1n}\exp(i\Phi_{1n})|]^2\} \quad (20)$$

where $\tilde{\rho}_{2m\alpha}$ is the amplitude distribution of the sample plane $\alpha$th. This one can be selected previously in an arbitrary manner. $W(\alpha)$ is a normalized weighting factor.

Different iterative calculation methods, such as the so-called "gradient-conjugates", "Gerchberg-Saxton" or "Adjacent Sequence Iteration Method (ASIM)" methods can be used for calculating solutions in a way that phase $\Phi$ minimizes error E.

These methods generally produce a fast convergence. It consists of iterative numeric calculation methods such as:

$$\Phi^{k+1} = \Phi^k + \tau d_k \quad (21)$$

With $\Phi$ for the phase, $\tau$ for the step and d for the iteration direction $k^{th}$. A phase will be selected to initiate the method.

The phase data are sought to be continuous (they are modulo $2\pi$) and are converted into geometrical data to define a diffractive phase element by the following relation:

$$t(r) = \frac{\lambda \Phi(r)}{2\pi(n-1)} \quad (22)$$

In practice, the gradient-conjugates method would rather be used.

An algorithm is then used that allows coefficients defining the profile of an aspheric surface similar to the diffractive structure DPE to be obtained, by approximating the phase distribution to a polynomial development that will provide the coefficients required to the definition of an equivalent aspheric surface.

Figure 8:
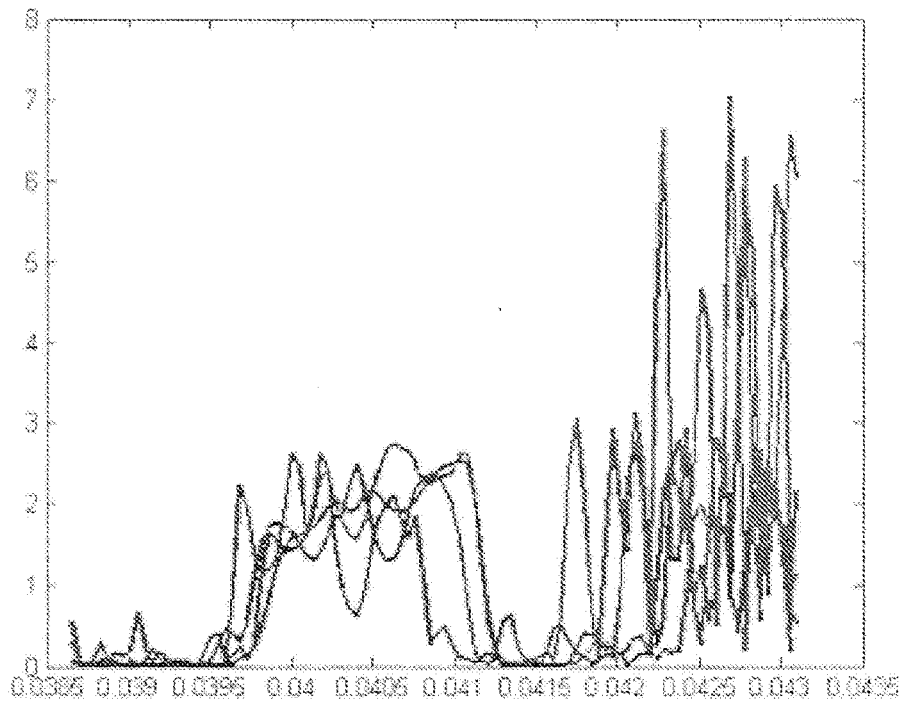
FIG. 8 is an example of the intensity distribution on the image side obtained with a lens according to this invention; the x-axis are in m and the y-axis intensities are arbitrary.

The performances of the diffractive phase element DPE and the hybrid lens obtained by the juxtaposition of this diffractive structure and the base optical corrective element can therefore be calculated and possibly optimized with a ray tracing program such as Zemax (or others). The following parameters are then obtained: modulation transfer function MTF; dimensions of one point image, "Point-Spread Function PSF", aberrations with Zernike or Seidel coefficients, etc. Each of these aspheric surfaces can be negative or positive. The optical corrective element can present all types of shapes. Combinations such as: convex-concave, concave-convex, convex-convex, concave-concave can also be calculated and constructed. The hybrid lens can thus be positive, negative or have complex shape, such as for example a toric shape. FIG. 8 gives an example of intensity calculated by the above mentioned method on one window.

The structure of the phase element DPE can be calculated in the eye with a model for the eye, for instance the one defined in the ISO standard 11979-2 or an adequate transfer function can be defined.

The resolution of the pseudo-phakic eye depends on the aspheric surface definition for obtaining a negative spherical aberration that will compensate the positive spherical aberration of the cornea. In this case, the eye-lens system will have a very good resolution/modulation transfer function MTF, may be limited by the retina or by the ocular elements, but not by the hybrid lens. Outside of the eye, the hybrid lens gives a poor resolution, which is improved following human implantation after combination with the visual system.

The phase element structures DPE allow the intended depths of focus to be obtained. The light beam, on the image side will be a cross-sectional light beam almost constant on one window. This length light of the beam in each segment corresponds to a depth of focus FD and therefore also to a selected depth of field. These selections allow for example to avoid the wearing of glasses following implantation of an intraocular lens IOL, or ensure that the patient can see correctly without glasses or contact lens CL.

The segmentation of the depths of focus with windows (or segments) allows the creation of a bifocal or trifocal lens or more, and generally multi-area and multifocal lenses. Each segment is independently controllable with regards to its depth of focus and its intensity. The diffractive/aspheric structure of the considered area of the lens surface allows the control of the desired depth on the considered segment.

Figure 5:
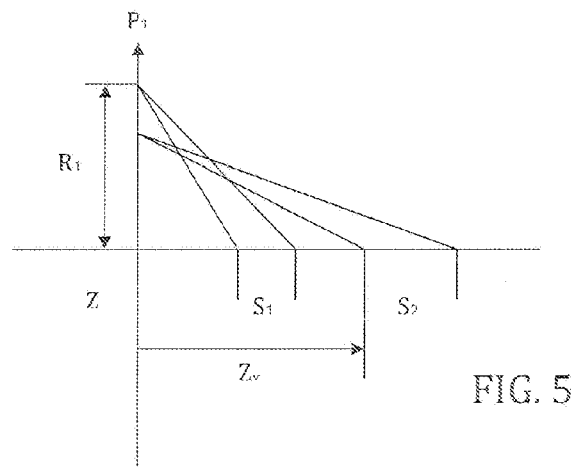
FIG. 5 shows the segmentation (windows) and the depth of focus according to this invention.

A diffractive phase element DPE/aspheric surface can be constructed on a lens surface, for example on the central part so as to provide a selected depth of focus of the light rays of this region (FIG. 5). The diffractive phase element DPE/aspheric surface can further be constructed on the peripheral area of the lens and provide a selected depth of focus of the light rays of this region. This depth of focus can be a dioptre fraction, 1 D or more. These selections determine the paraxial fp and marginal fm focal lengths that can therefore be obtained as follows:

$fp<fm$ or $fp>fm$

This depth of focus is much larger, as mentioned above, than conventional lenses (refractive, diffractive and others) because the phase mask creates PNDBs with unique propagation characteristics.

The paraxial and marginal powers are in an inverted relation to the focal lengths.

Figure 6A:
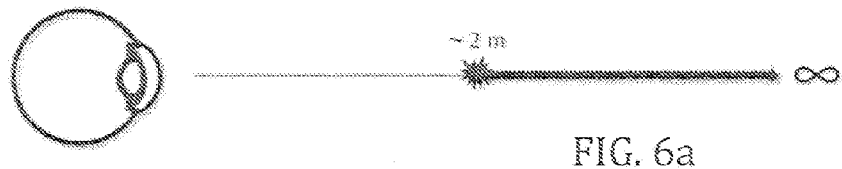
FIG. 6*a* represents an example of the depth of field obtained with a mono-focal ophthalmic lens of the prior art.
Figure 6B:
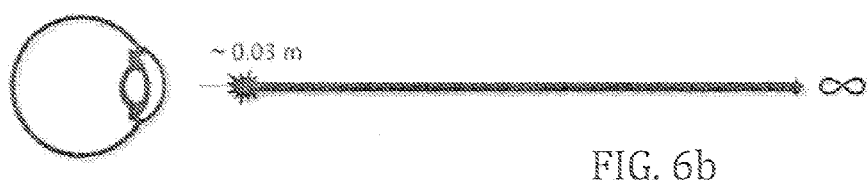
FIG. 6*b* represents an example of depth of field obtained with an ophthalmic lens according to the invention.

The depth of focus for near vision can be increased in a substantial manner. That of far vision can often be maintained given that it is often large. Such a combination will allow for an important depth of focus with a significant single window. This is represented by FIG. 6b.

The intensities in the different windows are dependent on the concerned area surfaces and can be selected. For example, the intensity in the near vision area can be increased in detriment of the far vision. The collection of light by the lens depends on its relative opening (focal length/effective diameter). By selecting the dimension of the different areas, the segment luminosity is defined. One of these can be increased in detriment of the other according to the desired requirements.

Figure 7:
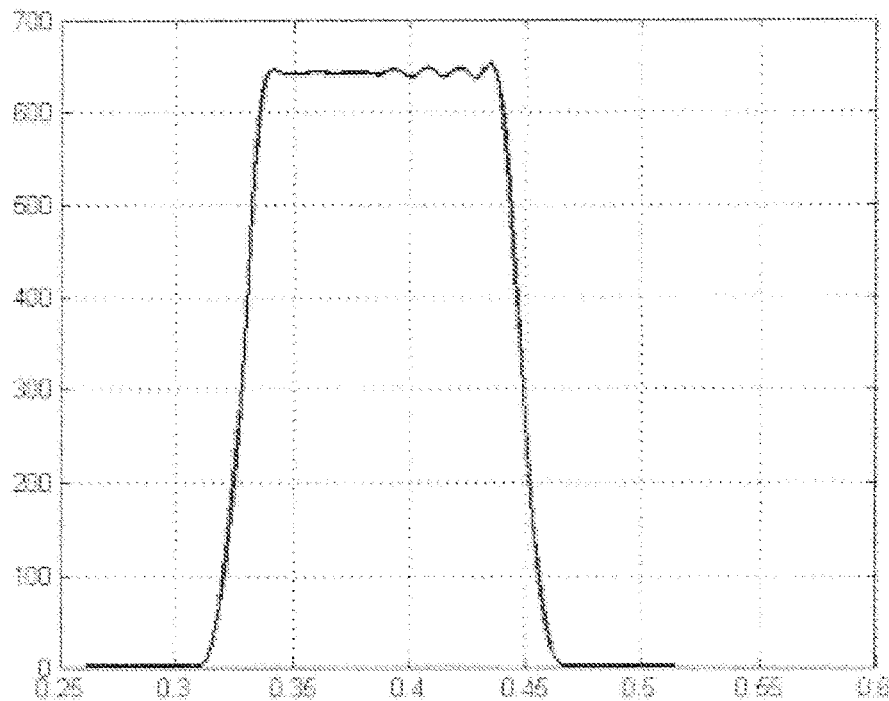
FIG. 7 represents an example of the depth of focus created by the diffractive phase element alone such as the one used in the present invention; the x-axis are in m and the y-axis intensities are arbitrary.

The central area can be used to provide a depth of focus of near space or far space images or inversely the peripheral area can be used to create a depth of focus of near space or far space images. All the combinations are possible. The different areas of the considered lens surface can also be created in sliding form, namely that when starting from the centre or from the periphery, it is possible to create depths of focus for increasingly distant space regions. The different depths of focus are flexible so as to obtain variable intensities for example of 40% for a near image and of 60% for a far image or inversely. All intensity distributions are achievable. Generally, the intensity distribution between the different areas will be controlled by the relative surfaces of these different areas. The depth of focus will allow the intensity distributions of each focal region to be controlled separately. The width of each area is therefore selected according to the considered problem. FIG. 7 discloses an example of depth of focus obtained with a single diffractive phase element. The x-axis are in m and the y-axis intensities are arbitrary. FIG. 8 shows the corresponding intensities as well as the depth of focus of a lens calculated and realized with the method disclosed in this invention. As in the case of FIG. 7, in FIG. 8, x-axis are in m and y-axis intensities are arbitrary.

For example, to correct the eyesight of an older person who no longer drives vehicles, their near vision can be favoured in detriment of his far vision for example with 65% of the light in the near segment, that will thus provide a good resolution/MTF. This near field segment extends from 30 cm to 1 m approximately. The intermediate and far vision will be lower, but still appreciable.

To correct the presbyopia of a younger person, a light distribution of 50/50% will be provided with an important near depth of focus at the centre of the lens and possibly no depth of focus for the far vision, or a non-existent power at the periphery since the presbyopic sight is satisfactory in an intermediate and remote distance.

The invention claimed is:

1. A method for making an ophthalmic lens with a configuration to correct a visual acuity of a user comprising:
   determining a shape of a base optical corrective element according to at least one of the following parameters:
   a desired power of the ophthalmic lens;
   a desired resolution or modulation transfer function;
   a desired extent of correction of the spherical aberrations of said ophthalmic lens;
   a desired extent of correction of the spherical aberrations of the cornea of the user;
   a desired extent of correction of the chromatic aberrations of said ophthalmic lens;
   a desired extent of correction of the chromatic aberrations of a cornea of the user; and
   a desired extent of correction of high order aberrations;
   determining a profile of a phase element structure comprising the steps of
   defining a desired depth of focus of said ophthalmic lens;
   calculating a desired phase distribution to be created at the entrance pupil of the lens from the desired depth of focus, said step of calculating the phase distribution further comprising the steps of:
   selecting a known phase distribution; and
   performing an iterative calculation to obtain said desired depth of focus;
   finding the phase which minimizes the differences between the effective phase distribution and the desired phase distribution;
   converting the phase which minimizes the difference between the effective phase distribution and the desired phase distribution into geometrical data to define a profile of the phase element structure; and
   juxtaposing the phase element structure and the base optical corrective element.

2. The method of claim 1, further comprising the step of forming a lens with the juxtaposed phase element structure and base optical corrective element.

3. The method according to claim 2, wherein the phase element structure is an aspheric refractive element that generates a phase distribution similar to the desired phase distribution.

4. The method of claim 2, wherein the phase element structure is a diffractive phase element.

5. The method according to claim 2, wherein the shape of said base optical corrective element is determined by at least two distinct lens areas and wherein the profile of said phase element structure is determined by at least one lens area.

6. The method according to claim 2, wherein the shape of said base optical corrective element is determined by at least two distinct lens areas, wherein the profile of said phase element structure is determined by the said at least two distinct lens areas, and wherein said distinct lens areas have a different depth of focus.

7. The method according to claim 6, wherein said at least two distinct lens areas have a similar modulation transfer function.

8. The method according to claim 2, wherein a depth of focus is selected for increasing the near vision of the user.

9. A lens made by the method of claim 2.

10. A lens made by the method of claim 1.

11. A method for making an ophthalmic lens with a configuration to correct a visual acuity of a user comprising:
   determining a shape of a base optical corrective element according to at least one of the following parameters:
      a desired power of the ophthalmic lens;
      a desired resolution or modulation transfer function;
      a desired extent of the correction of the spherical aberrations of said ophthalmic lens;
      a desired extent of the correction of the spherical aberrations of the cornea of the user;
      a desired extent of the correction of the chromatic aberrations of said ophthalmic lens;
      a desired extent of the correction of the chromatic aberrations of the cornea of the user; and
      a desired extent of the correction of high order aberrations;
   determining a profile of a phase element structure comprising the steps of
      defining a desired depth of focus of said ophthalmic lens;
      calculating a desired phase distribution to be created at the entrance pupil of the lens from the desired depth of focus;
      finding the phase which minimizes the differences between the effective phase distribution and the desired phase distribution;
      converting the phase which minimizes the difference between the effective phase distribution and the desired phase distribution into geometrical data in order to define the profile of the phase element structure, said step of converting the phase data further comprising the step of approximating by means of a polynomial distribution; and
   juxtaposing the phase element structure and the base optical corrective element.

12. The method of claim 11, further comprising the step of forming a lens with the juxtaposed phase element structure and base optical corrective element.

13. The method according to claim 12, wherein the phase element structure is an aspheric refractive element that generates a phase distribution similar to that of said diffractive structure.

14. The method of claim 12, wherein the phase element structure is a diffractive phase element.

15. The method according to claim 12, wherein the shape of said base optical corrective element is determined by at least two distinct lens areas and wherein the profile of said diffractive phase distribution structure is determined by at least one lens area.

16. The method according to claim 12, wherein the shape of said base optical corrective element is determined by at least two distinct lens areas, wherein the profile of said diffractive phase distribution structure is determined by the said at least two distinct lens areas, and wherein said distinct lens areas have a different depth of focus.

17. The method according to claim 16, wherein said at least two distinct lens areas have a similar modulation transfer function.

18. The method according to claim 12, wherein a depth of focus is selected for increasing the near vision of the user.

19. A lens made by the method of claim 12.

20. A lens made by the method of claim 11.

* * * * *